United States Patent [19]
Takano

[11] Patent Number: 5,168,878
[45] Date of Patent: Dec. 8, 1992

[54] MECHANICAL SCAN TYPE ULTASONIC PROBE

[75] Inventor: Masayuki Takano, Ootawara, Japan

[73] Assignee: Kabushiki Kaisha Toshiba, Kawasaki, Japan

[21] Appl. No.: 680,934

[22] Filed: Apr. 5, 1991

[30] Foreign Application Priority Data

Apr. 6, 1990 [JP] Japan .................. 2-92713
Apr. 6, 1990 [JP] Japan .................. 2-92714

[51] Int. Cl.$^5$ ............................. A61B 8/12
[52] U.S. Cl. ...................... 128/662.06; 128/660.10; 128/660.09
[58] Field of Search ............ 128/660.07, 660.08, 128/660.09, 660.10, 662.05, 662.06; 73/861.25, 633, 634, 635, 623

[56] References Cited

U.S. PATENT DOCUMENTS

| | | | |
|---|---|---|---|
| 3,443,433 | 5/1969 | Liston et al. | 128/662.06 |
| 4,688,576 | 8/1987 | Meyers | 128/660.10 |
| 4,732,156 | 3/1988 | Nakamura | 128/660.09 |
| 4,893,628 | 1/1990 | Angelsen | 128/660.09 |
| 4,899,757 | 2/1990 | Pope, Jr. et al. | 128/662.06 |
| 4,991,588 | 2/1991 | Pflueger et al. | 128/662.06 |

Primary Examiner—Kyle L. Howell
Assistant Examiner—George Manuel
Attorney, Agent, or Firm—Oblon, Spivak, McClelland, Maier & Neustadt

[57] ABSTRACT

A mechanical scan type ultrasonic probe is disclosed, in which a rotational force transmitting shaft for transmitting the rotational force of a motor to an ultrasonic transducer, and a guide pipe for guiding the rotational force transmitting shaft are improved. The guide pipe is a spiral spring. The rotational force transmitting shaft is a highly conductive double spiral spring. Since the guide pipe is constituted by a spiral spring, the pipe can follow any bending movement of the rotational force transmitting shaft to guide the shaft. In addition, since the rotational force transmitting shaft is constituted by a highly conductive double spiral spring, it can properly supply and extract electrical signals to and from an ultrasonic transducer, and can properly transmit the rotational force to the transducer.

23 Claims, 5 Drawing Sheets

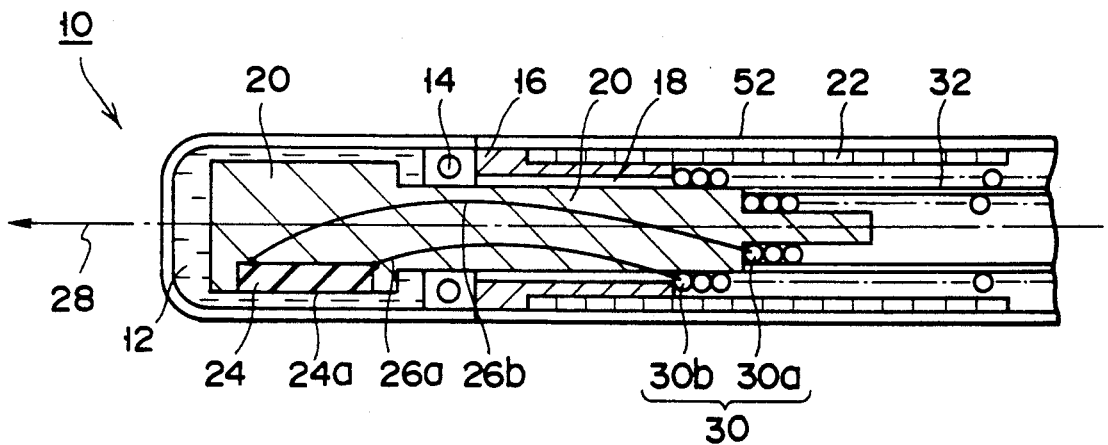
FIG. 4
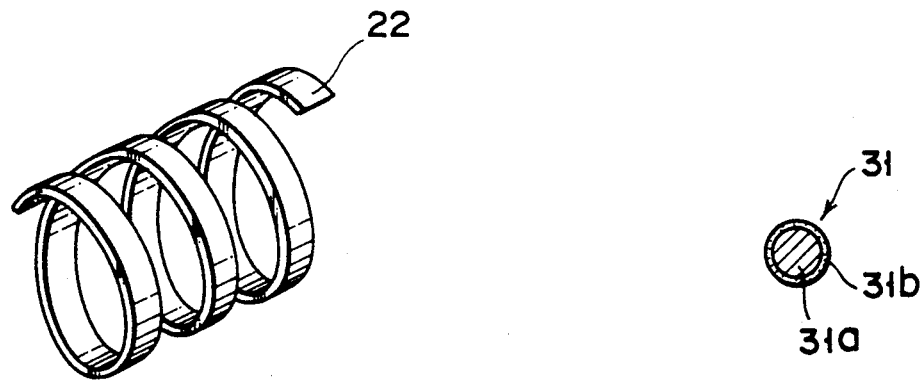
FIG. 5
FIG. 6

MECHANICAL SCAN TYPE ULTASONIC PROBE

BACKGROUND OF THE INVENTION

1. Field of the Invention

The present invention relates a mechanical scan type ultrasonic probe for performing mechanical scanning of an ultrasonic beam with respect to an object to be examined.

2. Description of the Related Art

A conventional mechanical scan type ultrasonic probe of this type will be described below with reference to FIG. 1. FIG. 1 is a sectional view showing a body cavity mechanical scan type ultrasonic probe used for diagnosis of the interior of a body cavity, e.g., the gullet, the intestines, a blood vessel, and the like in an object to be examined. This probe is disclosed in Published Examined Japanese Patent Application No. 63-34737.

As shown in FIG. 1, the rotational force of a motor 100 as a rotating means is transmitted to a rotating shaft 106 through gears 102 and 104. This rotational force is transmitted from the rotating shaft 106 to a rotor 110 through a rotational force transmitting shaft 108 constituted by a multiple spiral spring. Since the rotational force transmitting shaft 108 is constituted by the multiple spiral spring, it has both flexibility and expandability and can efficiently transmit a rotational force. The rotational force transmitting shaft 108 shown in FIG. 1 is constituted by a double spiral spring as an example. The rotor 110 is arranged in the internal space of an inserting portion 10 to be inserted in a body cavity (not shown). An ultrasonic transducer 112 is arranged on an end portion of the rotor 110. With this arrangement, the ultrasonic transducer 112 is rotated integrally with the rotor 110. One end of each of a pair of signal lines 114a and 114b is connected to a corresponding one of rotating terminals 116a and 116b, which are rotated integrally with the rotating shaft 106, through a hollow portion 108a of the rotational force transmitting shaft 108. The other end of each of the pair of signal lines 116a and 116b is connected to the transducer 112. With this arrangement, the pair of signal lines 116a and 116b are also rotated integrally with the transducer 112. In this arrangement, supply of a driving signal to the transducer 112 and extraction of an echo signal received by the transducer 112 are performed by a slip ring mechanism constituted by the rotating terminals 116a and 116b and fixed terminals 118a and 118b.

The rotational force transmitting shaft 108 constituted by the double spiral spring is guided into a pipe-like guide 120 to retain its shape. In some cases, however, the rotational force transmitting shaft 108 cannot exhibit sufficient expandability because of friction with the pipe-like guide 120 depending on how the shaft 108 is bent. As a result, the rotor 110 may not be smoothly rotated.

In order to eliminate such a drawback, the pipelike guide 120 or the rotational force transmitting shaft 108 is designed to be axially slidable. This arrangement is disclosed in Published Unexamined Japanese patent Application No. 61-64240. FIG. 2 shows an example of the above-mentioned arrangement, in which a metal fitting 124 having a flange 122 is connected to the distal end portion of a pipe-like guide 120. In addition, a cylindrical space portion 126 corresponding to the flange 122 is formed in an inserting portion 10 to constitute a slide mechanism. The metal fitting 124 is designed to be moved in a direction indicated by an arrow together with the flange 122 so as to allow the pipe-like guide 120 to freely slide in the axial direction.

In order to realize such a conventional arrangement, a complicated slide mechanism including a bearing is required. In addition, the pipe-like guide 120 may be distorted even when the rotational force transmitting shaft 108 is slightly bent. As a result, the friction between the rotational force transmitting shaft 108 and the pipe-like guide 120 is increased, and hence smooth transmission of a rotational force to the rotor 110 becomes difficult.

Furthermore, in the conventional mechanical scan type ultrasonic probe when the transducer 112 (rotor 110) is rotated at high speed, disconnection of the signal lines 114a and 114b tends to occur. More specifically, if the transducer 112 (rotor 110) is rotated at high speed while the rotational force transmitting shaft 108 constituted by the double spiral spring is bent, since a tension acts on the rotational force transmitting shaft 108, the signal lines 114a and 114b may be disconnected. In addition, since the rotational force transmitting shaft 108 is constituted by a spring, the signal lines 114a and 114b may be caught in the gap between turns of the spring and tend to be disconnected upon bending of the shaft 108 or by the friction between the shaft 108 and the pipe-like guide 120. Moreover, since the diameter of the hollow portion 108a of the rotational force transmitting shaft 108 is 1 mm at best, a cumbersome operation is required to insert the signal lines 114a and 114b into the space of the hollow portion 108a to a depth of 1 mm or more.

SUMMARY OF THE INVENTION

It is the first object of the present invention to provide a mechanical scan type ultrasonic probe including a pipe-like guide which can contract/expand in response to any bending movement of a rotational force transmitting shaft with a simple arrangement.

It is the second object of the present invention to provide a mechanical scan type ultrasonic probe in which a connecting structure of signal lines is improved to prevent disconnection of the signal lines.

In order to achieve the first object, according to the present invention, there is provided a mechanical scan type ultrasonic probe comprising:
rotating means;
rotational force transmitting means for transmitting a rotational force of the rotating means;
ultrasonic scan means which is rotated upon reception of the rotational force from the rotational force transmitting means;
housing means for housing the ultrasonic scan means; and
guide means for guiding the rotational force transmitting means,
wherein the guide means is constituted by a spiral spring.

In order to achieve the second object, according to the present invention, there is provided a mechanical scan type ultrasonic probe comprising:
rotating means;
rotational force transmitting means, constituted by a plurality of spiral springs, for transmitting a rotational force of the rotating means;

ultrasonic scan means which is rotated upon reception of the rotational force from the rotational force transmitting means;

housing means for housing the ultrasonic scan means; and guide means for guiding the rotational force transmitting means, wherein the plurality of spiral springs of the rotational force transmitting means are electrically connected to at least the ultrasonic scan means to supply and extract an electrical signal to and from the ultrasonic scan means.

In order to achieve the first and second objects, according to the present invention, there is provided a mechanical scan type ultrasonic probe comprising:

rotating means;

rotational force transmitting means, constituted by a plurality of spiral springs, for transmitting a rotational force of the rotating means;

ultrasonic scan means which is rotated upon reception of the rotational force from the rotational force transmitting means;

housing means for housing the ultrasonic scan means; and guide means for guiding the rotational force transmitting means, wherein the guide means is constituted by a spiral spring, and the plurality of spiral springs of the rotational force transmitting means are electrically connected to at least the ultrasonic scan means to supply and extract an electrical signal to and from the ultrasonic scan means.

Additional objects and advantages of the invention will be set forth in the description which follows, and in part will be obvious from the description, or may be learned by practice of the invention. The objects and advantages of the invention ma be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is an enlarged sectional view showing an inserting portion in FIG. 3;

FIG. 5 is a perspective view showing a pipe-like guide in FIGS. 3 and 4;

FIG. 6 is a sectional view showing a wire material for a conductive double spiral spring in FIGS. 3 and 4.

DETAILED DESCRIPTION OF THE PREFERRED EMBODIMENTS

Embodiments of the present invention will be described below with reference to the accompanying drawings.

Figure 1:
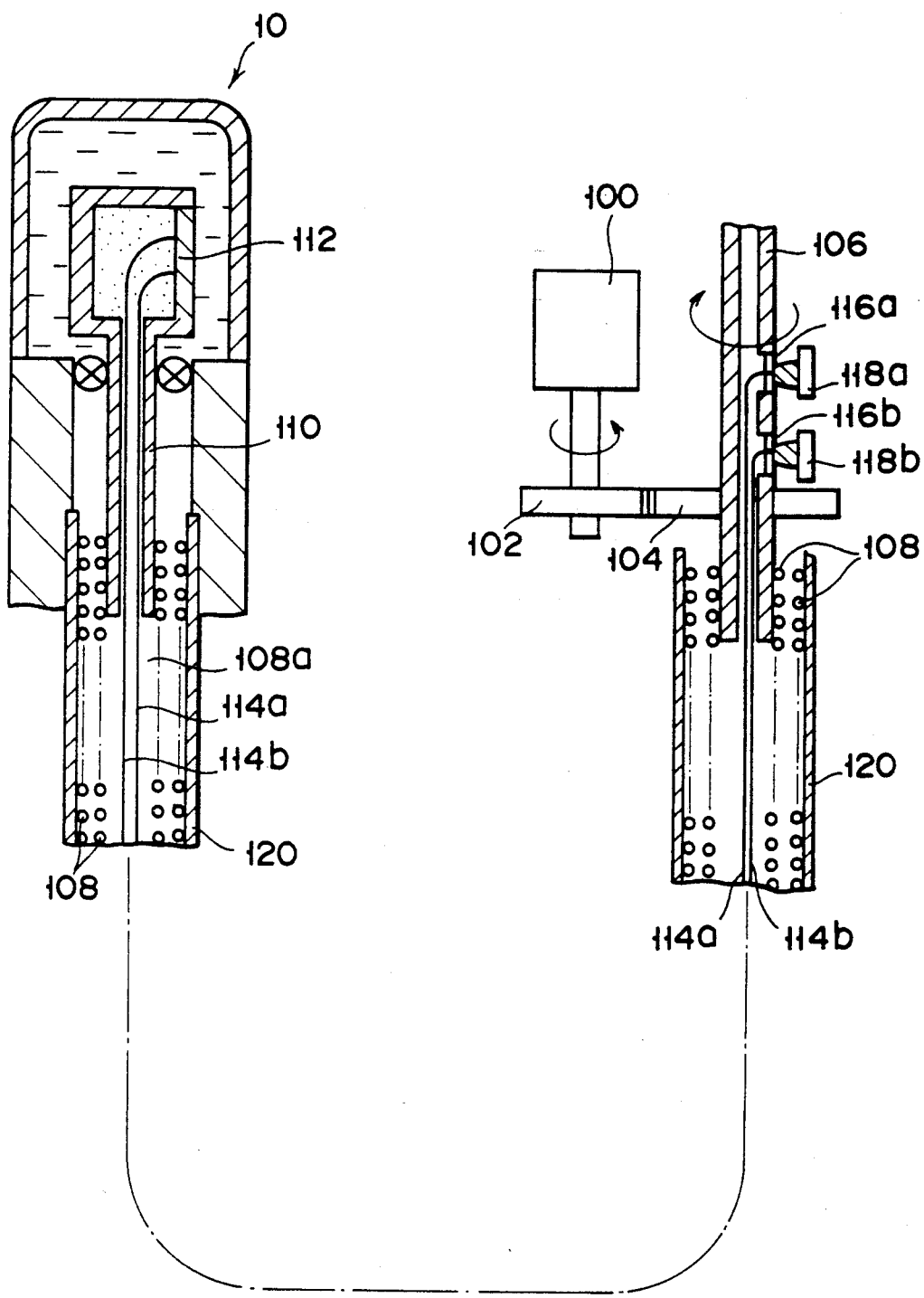
FIG. 1 is a sectional view showing a main part of a conventional mechanical scan type ultrasonic probe.
Figure 2:
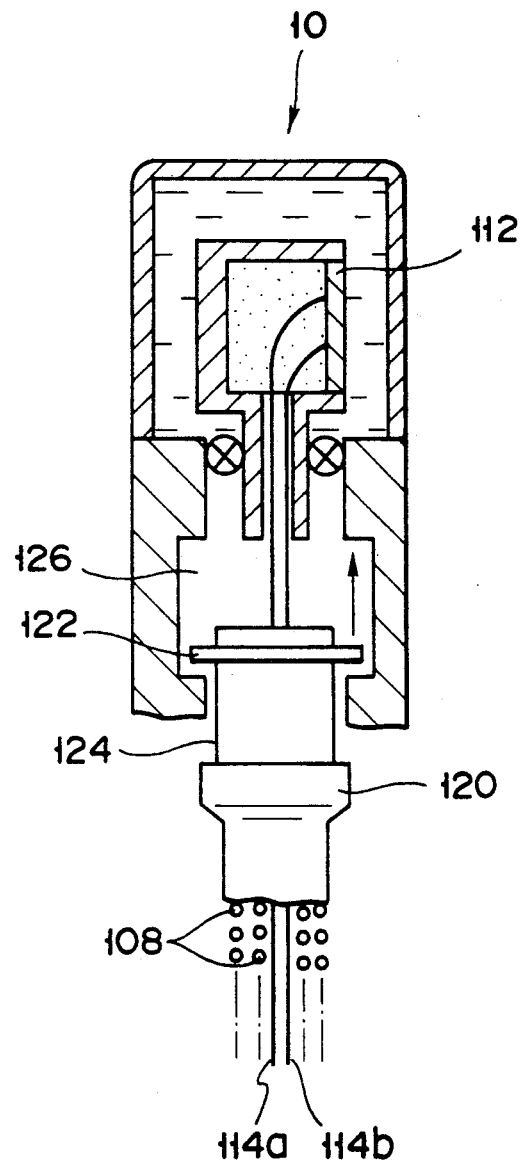
FIG. 2 is a sectional view showing another conventional mechanical scan type ultrasonic probe.
Figure 3:
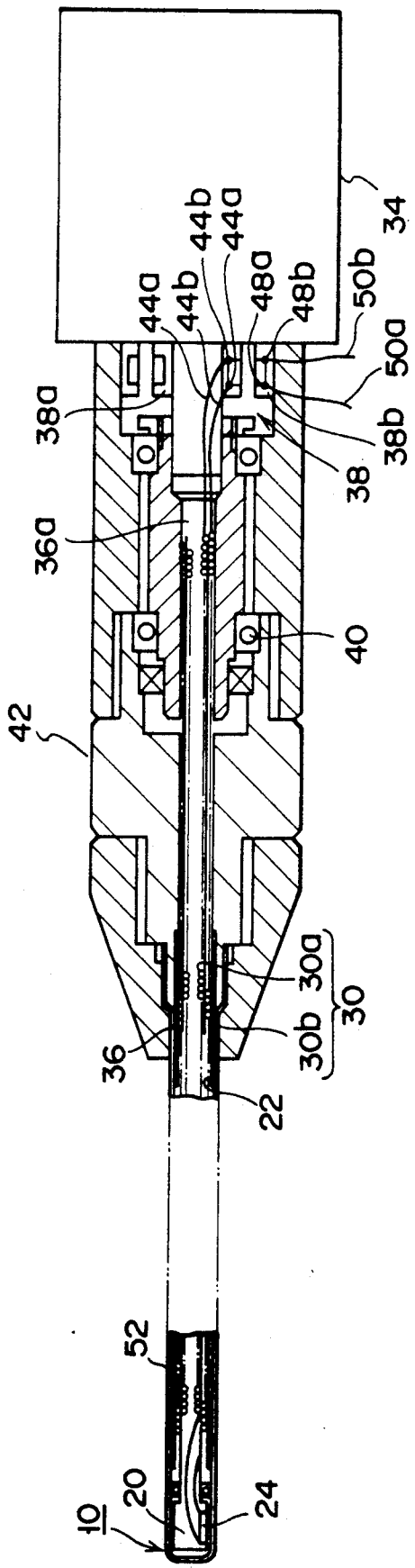
FIG. 3 is a sectional view showing a mechanical scan type ultrasonic probe according to the first embodiment of the present invention.

Referring to FIGS. 3 and 4, reference numeral 10 denotes an inserting portion to be inserted in a body cavity (not shown). This inserting portion 10 is formed into a cap-like shape so as to store a liquid ultrasonic transmission medium 12 therein. The inserting portion 10 is designed to house an ultrasonic scan means (to be described later) constituted by a rotor 20 and an ultrasonic transducer 24. A side surface of the inserting portion 10 constitutes an ultrasonic window. Therefore, at least the portion, of the inserting portion 10, which constitutes the ultrasonic window is composed of an ultrasonic-transmitting material having excellent acoustic characteristics. In addition, a cylindrical inserting portion base pipe 16 is arranged on the opening side of the inserting portion 10 through a bearing 14. A seal pipe 18 is arranged in the inserting portion base pipe 16. The seal pipe 18 serves to prevent the liquid ultrasonic transmission medium 12 from leaking out from the internal space of the inserting portion 10.

The rotor 20 is arranged in the internal spaces of the inserting portion 10 and the inserting portion base pipe 16 through the bearing 14 and the seal pipe 18. One opening side of a guide spring 22 shown in FIG. 5 is attached to the other side of the inserting portion base pipe 16. This guide spring 22 is formed by, e.g., spirally winding a flat spring member. The guide spring 22 is formed as a spring mechanism and hence can freely contract/expand in response to any bending movement of a rotational force transmitting shaft 30. The thickness of the guide spring 22 is set to be, e.g., about 0.5 mm, which is larger than that of the rotational force transmitting shaft 30 by about 0.2 mm. By setting the size of the guide spring 22 in this manner, both the guiding characteristics of the guide spring 22 with respect to the rotational force transmitting shaft 30 and the rotational force transmission characteristics of the shaft 30 can be made effective. Although FIG. 5 shows the guide spring 22 as if there are gaps between the adjacent turns, there are almost no gaps in practice.

The ultrasonic transducer 24 is arranged on one end of the rotor 20. The ultrasonic transducer 24 is placed on a side wall of the rotor 20 such that an ultrasonic transmission/reception surface 24a is located in a direction perpendicular to an axial direction 28 of the inserting portion 10. A pair of signal lines 26a and 26b are embedded in the rotor 20. One end of each of the signal lines 26a and 26b is connected to the ultrasonic transducer 24, while the other end of each extends through the other end of the rotor 20. Since the inserting portion 10 is filled with the liquid ultrasonic transmission medium 12, an ultrasonic wave emitted from the ultrasonic transmission/reception surface 24a of the ultrasonic transducer 24 is transmitted through the liquid ultrasonic transmission medium 12 and the ultrasonic window as the side wall of the inserting portion 10, and is radiated outside the inserting portion 10. A reflected ultrasonic wave is transmitted through the ultrasonic window as the side wall of the inserting portion 10 and the liquid ultrasonic transmission medium 12, and reaches the ultrasonic transmission/reception surface 24a of the ultrasonic transducer 24. Therefore, when the ultrasonic transducer 24 is driven for transmission while the rotor 20 is rotated, ultrasonic waves are radially emitted in a direction perpendicular to the axial direction 28 of the inserting portion 10. In this case, if the entire side wall of the inserting portion 10 is formed into an ultrasonic window, radial scanning is realized. If a portion of the side wall of the inserting portion 10 is formed into an ultrasonic window, sector scanning is realized.

One end of the rotational force transmitting shaft 30 is fixed to the other end of the rotor 20. The rotational force transmitting shaft 30 is constituted by a multiple spiral spring formed by alternately winding a plurality of wires consisting of a spring material in opposite directions. More specifically, the rotational force transmitting shaft 30 shown in FIGS. 3 and 4 is constituted by a double spiral spring formed by concentrically stacking a first spiral spring 30a and a second spiral spring 30b. The second spiral spring 30b is formed by winding a wire consisting of a spring member in a direction opposite to the winding direction of the first spiral spring 30a. FIG. 6 is a sectional view of one wire of the rotational force transmitting shaft 30. As is apparent from FIG. 6, a wire 31 is formed by coating a highly conductive member 31b, e.g., copper, on a spring member 31a having a circular cross section. Since the rotational force transmitting shaft 30 is constituted by the double spiral spring, it has both flexibility and expandability. With the rotational force transmitting shaft 30 having such a structure, high torsional rigidity can be ensured even during the rotation of the shaft 30. Therefore, the rotational force of the rotational force transmitting shaft 30 can be accurately transmitted to the rotor 20. In addition, since the rotational force transmitting shaft 30 has excellent flexibility, the shaft can be properly bent in accordance with an inserting state of the inserting portion 10 in a body cavity. Furthermore, since the rotational force transmitting shaft 30 is inserted in the guide spring 22, the shape of the shaft 30 can be maintained by the guide spring 22. Moreover, since the rotational force transmitting shaft 30 consists of the wire formed by coating the highly conductive member 31b on the spring member 31a, the shaft 30 is suitable for transmission/reception of electrical signals.

The other end of each of the pair of signal lines 26a and 26b, each having one end connected to the ultrasonic transducer 24, is connected to a corresponding one of the first and second spiral springs 30a and 30b of the rotational force transmitting shaft 30. An insulating pipe 32 consisting of a flexible insulating member such as PTFE is inserted between the first and second spiral springs 30a and 30b of the rotational force transmitting shaft 30 so as to electrically insulate the first and second spiral springs 30a and 30b from each other.

As shown in FIG. 3, the rotational force transmitting shaft 30 is connected to a rotating shaft of a motor 34 as a rotating means. More specifically, the motor 34 has a hollow rotating shaft 36. The first spiral spring 30a of the rotational force transmitting shaft 30 is fixed to the inner wall of a hollow portion 36a of the rotating shaft 36. The second spiral spring 30b of the rotational force transmitting shaft 30 is fixed to the outer wall of the hollow portion 36a of the rotating shaft 36. With this arrangement, the rotational force of the motor 34 is transmitted to the rotational force transmitting shaft 30 as the double spiral spring. Therefore, the rotor 20 and the transducer 24 can be integrally rotated. A rotating transformer constituted by a rotor 38a, a bearing 40, and a stator 38b is arranged on the hollow rotating shaft 36 of the motor 34. The rotor 38a is fixed to the hollow rotating shaft 36. The stator 38b is supported by a frame 42. The other end of the guide spring 22 is fixed to the frame 42. End portions of the first and second spiral springs 30a and 30b of the rotational force transmitting shaft 30 are respectively connected to rotor terminals 44a and 44b of a rotating transformer 38 through a pair of signal lines 44a and 44b. A pair of signal lines 50a and 50b respectively extend from stator terminals 48a and 48b of the rotating transformer 38. This pair of signal lines 50a and 50b are connected to an ultrasonic transmission/reception circuit (not shown). Note that reference numeral 52 denotes a cover, consisting of a flexible material, for covering the inserting portion 10 and the guide spring 22.

An operation of this embodiment will be described below. The rotational force of the motor 34 is transmitted from the rotating shaft 36 to the rotor 20 through the rotational force transmitting shaft 30. As a result, the transducer 24 is rotated integrally with the rotor 20. At this time, a driving signal output from the ultrasonic transmission/reception circuit (not shown) is transmitted to the signal lines 44a and 44b of the rotor 38a through the signal lines 50a and 50b of the stator 38b by magnetic coupling. The driving signal is then transmitted to the signal lines 26a and 26b through the first and second spiral springs 30a and 30b constituting the rotational force transmitting shaft 30. With this operation, the driving signal is supplied to the transducer 24. As a result, the transducer 24 generates an ultrasonic wave from the ultrasonic transmission/reception surface 24a, thus performing desired ultrasonic scanning.

An echo signal from an object to be examined is received by the transducer 24. Subsequently, the echo signal is transmitted to the ultrasonic transmission/reception circuit in a reverse sequence to that in the generation of the ultrasonic wave described above. That is, the echo signal is transmitted from the transducer 24 to the signal lines 44a and 44b through the signal lines 26a and 26b and the first and second spiral springs 30a and 30b, and is subsequently supplied to the ultrasonic transmission/reception circuit through the signal lines 50a and 50b of the rotor 38a by magnetic coupling.

According to this embodiment, since the guide spring 22, which serves to guide the rotational force transmitting shaft 30, has a spring effect, the spring 22 can properly contract/expand in response to any bending movement of the shaft 30, regardless of the manner of bending the shaft 30 in accordance with a state of diagnosis. That is, the guide spring 22 is not distorted upon bending of the rotational force transmitting shaft 30, unlike the conventional structure. Since the friction between the spring 22 and the shaft 30 is not increased, the rotational force can be smoothly transmitted to the transducer 24. In addition, since no slide mechanism is necessary, and only a coil-like wire is required, the objects of the present invention can be achieved with a simple arrangement. Note that the guide spring 22 is not limited to a metal wire as long as it has a spring effect. In addition, the sectional shape of the guide spring 22 is not limited to a rectangular shape, and various shapes can be employed.

In addition, according to this embodiment, when supply of a driving signal to the transducer 24 and extraction of an echo signal received by the transducer 24 are performed in this manner, the first and second spiral springs 30a and 30b of the rotational force transmitting shaft 30 for transmitting the rotational force of the motor 34 to the transducer can be used as signal lines. With this arrangement, no special signal lines are required, and there is no possibility that signal lines receive tension or are caught in the gap between turns of the spring during high-speed rotation of the shaft 30. This prevents disconnection of the signal lines. Furthermore, since there is no need to perform a cumbersome operation of inserting signal lines into the hollow portion 23a, the assembly efficiency of an ultrasonic probe can be improved.

In the above-described embodiment, a double spiral spring is used as signal lines. However, the present invention is not limited to this, and a multiple spring having three or more spring components can be used. In this case, if springs used as signal lines are insulated from each other, no problems are posed.

Figure 7:
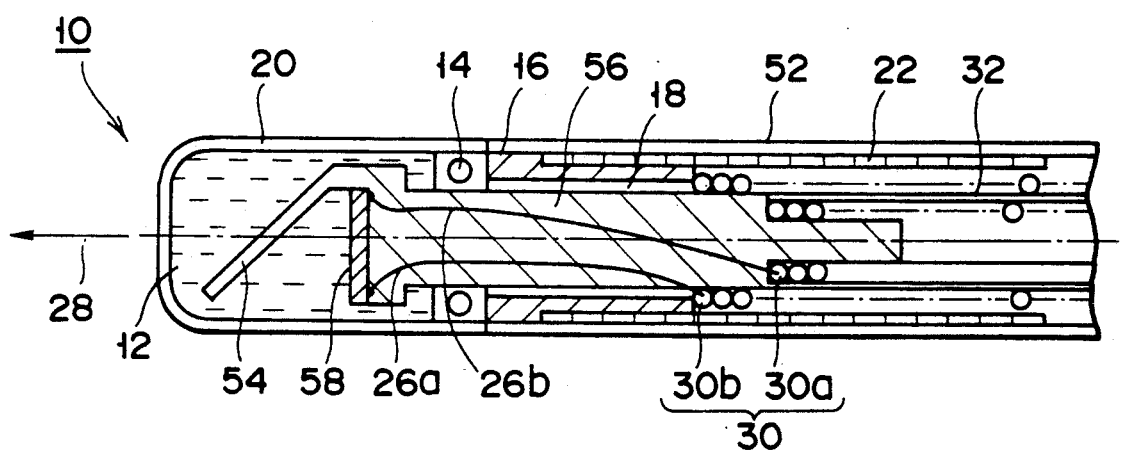
FIG. 7 is a sectional view showing a mechanical scan type ultrasonic probe according to the second embodiment of the present invention.

FIG. 7 is a sectional view of a mechanical scan type ultrasonic probe including a rotor 56 having a reflector 54. In this embodiment, an ultrasonic transducer 58 is arranged on an end portion of the rotor 56 such that the transmission/reception surface of the transducer 58 is parallel to an end face of the rotor 56 in the axial direction. Since the inclined reflector 54 is fixed to the end portion of the rotor 56, ultrasonic waves can be radially emitted in a direction perpendicular to a axial direction 28 of an inserting portion 10.

What is claimed is:

1. A mechanical scan type ultrasonic probe comprising:
    a rotational force generating unit for generating a rotational force;
    a rotational force transmitting shaft which has both flexibility and expandability, for transmitting said rotational force of said rotational force generating unit;
    an ultrasonic scan unit which is rotated upon reception of the rotational force from said rotational force transmitting shaft and fixed to an end portion of said rotational force transmitting shaft;
    a housing unit for housing said ultrasonic scan unit therein; and
    a pipe like guide member which comprises a spiral spring member, for guiding said rotational force transmitting shaft inserted therein.

2. The probe according to claim 1, wherein said rotational force transmitting shaft is constituted by a plurality of spiral springs.

3. The probe according to claim 2, wherein said spiral springs are two spiral springs isolated from each other by an insulation member.

4. The probe according to claim 1, wherein said rotational force transmitting shaft is constituted by two spiral springs which are an oppositional winding.

5. The probe according to claim 4, wherein said two spiral springs are isolated from each other by an insulation member.

6. The probe according to claim 1, wherein said ultrasonic scan unit includes a rotor for receiving the rotational force transmitted from said rotational force transmitting shaft, and an ultrasonic transducer fixed to one end portion of said rotor.

7. The probe according to claim 1, wherein said housing unit is adapted to be inserted in a body cavity of an object to be examined.

8. The probe according to claim 1, wherein said housing unit has an ultrasonic window for performing radial scanning.

9. The probe according to claim 1, wherein said housing unit has an ultrasonic window for performing sector scanning.

10. A mechanical scan type ultrasonic probe comprising:
    a rotational force generating unit for generating a rotational force;
    a rotational force transmitting shaft which is constituted by a plurality of spiral springs and has both flexibility and expandability, for transmitting said rotational force of said rotational force generating unit;
    an ultrasonic scan unit which is rotated upon reception of the rotational force from said rotational force transmitting shaft, fixed to an end portion of said rotational force transmitting shaft, and is connected to said plurality of spiral springs of said rotational force transmitting shaft to supply and extract an electrical signal to and from said ultrasonic scan unit;
    a housing unit for housing said ultrasonic scan unit therein; and
    a pipe like guide member for guiding said rotational force transmitting shaft inserted therein.

11. The probe according to claim 10, wherein said rotational force transmitting shaft is constituted by two spiral spring which are an oppositional winding.

12. The probe according to claim 10, wherein said ultrasonic scan unit includes a rotor for receiving the rotational force transmitted from said rotational force transmitting shaft, and an ultrasonic transducer fixed to one end portion of said rotor.

13. The probe according to claim 10, wherein said housing unit is adapted to be inserted in a body cavity of an object to be examined.

14. The probe according to claim 10, wherein said housing unit has an ultrasonic window for performing radial scanning.

15. The probe according to claim 10, wherein said housing unit has an ultrasonic window for performing sector scanning.

16. The probe according to claim 10, wherein said spiral springs of said rotational force transmitting shaft include two spiral springs which are isolated from each other by an insulation member.

17. A mechanical scan type ultrasonic probe comprising:
    a rotational force generating unit for generating a rotational force;
    a rotational force transmitting shaft which is constituted by a plurality of spiral springs and has both flexibility and expandability, for transmitting said rotational force of said rotational force generating unit;
    an ultrasonic scan unit which is rotated upon reception of the rotational force from said rotational force transmitting shaft, fixed to an end portion of said rotational force transmitting shaft, and is connected to said plurality of spiral springs of said rotational force transmitting shaft to supply and extract an electrical signal to and from said ultrasonic scan unit;
    a housing unit for housing said ultrasonic scan unit therein; and
    a pipe-like guide member which has a spiral spring member, for guiding said rotational force transmitting shaft inserted therein.

18. The probe according to claim 17, wherein said rotational force transmitting shaft is constituted by two spiral springs which are an oppositional winding.

19. The probe according to claim 17, wherein said ultrasonic force transmitted from said rotational force transmitting shaft, and an ultrasonic transducer fixed to one end portion of said rotor.

20. The probe according to claim 17, wherein said housing unit is adapted to be inserted in a body cavity of an object to be examined.

21. The probe according to claim 17, wherein said housing unit has an ultrasonic window for performing radial scanning.

22. The probe according to claim 17, wherein said housing unit has an ultrasonic window for performing sector scanning.

23. The probe according to claim 17, wherein said spiral springs of said rotational force transmitting shaft include two spiral springs which are isolated from each other by an insulation member.

* * * * *

UNITED STATES PATENT AND TRADEMARK OFFICE
CERTIFICATE OF CORRECTION

PATENT NO. : 5,168,878
DATED : December 8, 1992
INVENTOR(S) : Masayuki Takano It is certified that error appears in the above-identified patent and that said Letters Patent is hereby corrected as shown below:

On the title page, Item [54] and column 1, line 2, the title is incorrect, should read as follows:

--MECHANICAL SCAN TYPE ULTRASONIC PROBE--.

Signed and Sealed this

Nineteenth Day of October, 1993

*Attest:*

BRUCE LEHMAN

*Attesting Officer*        *Commissioner of Patents and Trademarks*